United States Patent [19]

Cross et al.

[11] 4,044,013

[45] Aug. 23, 1977

[54] 1,2-DIALKYLPYRAZOLIUM COMPOUNDS HAVING 3-(OR 3,5-) NITROGEN-CONTAINING HETEROCYCLIC GROUP

[75] Inventors: Barrington Cross, Rocky Hill; Bryant Leonidas Walworth, Pennington, both of N.J.

[73] Assignee: American Cyanamid Company, Stamford, Conn.

[21] Appl. No.: 683,562

[22] Filed: May 5, 1976

Related U.S. Application Data

[62] Division of Ser. No. 574,795, May 5, 1975, abandoned.

[51] Int. Cl.$^2$ .................. C07D 401/04; C07D 403/04
[52] U.S. Cl. .......................... 260/293.63; 260/239 B; 260/293.7; 71/92; 260/293.64; 548/374; 548/364; 548/365; 548/367; 548/363; 548/376; 548/377; 548/375
[58] Field of Search ................ 260/293.63, 293.7, 311, 260/239 B, 310 R, 293.64

[56] References Cited

U.S. PATENT DOCUMENTS

| 3,882,142 | 5/1975 | Walworth et al. | 260/311 |
| 3,963,741 | 6/1976 | Cross et al. | 260/311 |
| 3,963,742 | 6/1976 | Cross et al. | 260/311 |

OTHER PUBLICATIONS

Elquero et al., "Bull. Chim. Soc. France" (1972), No. 7, pp. 2807–2814.

*Primary Examiner*—Henry R. Jiles
*Assistant Examiner*—Robert T. Bond
*Attorney, Agent, or Firm*—Harry H. Kline

[57] ABSTRACT

There are provided 1,2-dialkylpyrazolium compounds having positioned thereon a 3- or 5-substituted nitrogen-containing heterocyclic group or 3,5-disubstituted nitrogen-containing heterocyclic groups as well as a method for preparing the same. There is also provided a method for the control of undesirable plant species with the above-identified compounds.

8 Claims, No Drawings

1,2-DIALKYLPYRAZOLIUM COMPOUNDS HAVING 3-(OR 3,5-) NITROGEN-CONTAINING HETEROCYCLIC GROUP

This is a divisional of application Ser. No. 574,795, filed May 5, 1975, now abandoned.

The present invention relates to herbicidal pyrazolium compounds which have a nitrogen containing heterocyclic group in either the 3 position, the 5 position or the 3 and 5 positions of the pyrazolium ring and are represented by the formula:

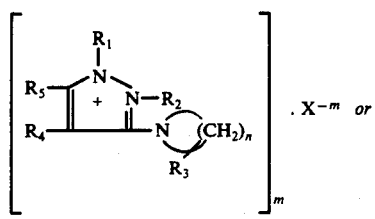

(I)

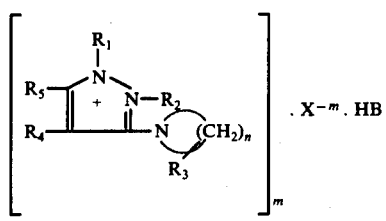

(II)

wherein $R_1$ and $R_2$ each represents alkyl $(C_1-C_4)$; $R_3$ is hydrogen, alkyl (1-3), alkoxy, aryl, aralkyl, cyano, carboxamido, or carboalkoxy; or $R_4$ represents hydrogen, alkyl $(C_1-C_4)$, alkoxy $(C_1-C_4)$, alkylsulfonyl or halogen; $R_5$ represents a member selected from the group consisting of

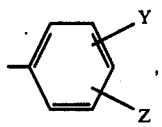

cycloalkyl $C_3-C_7$ and

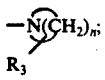

Y and Z each represents a member selected from the group consisting of hydrogen, halogen, methyl and alkoxy $(C_1-C_4)$; X represents an anion with a charge of 1 to 3; n represents an integer from 4 to 6; m represents an integer from 1 to 3; and HB represents an inorganic or organic acid.

As employed in the present application, the term "halogen" is intended to mean fluorine, chlorine, bromine and iodine. The fluoro, chloro, and bromo substituents are, however, preferred.

Illustrative of the anions that the suitable for use in the present invention are, for example, halides, such as chloride, bromide or iodine; acetate; sulfate; hydroxide; hydrogen sulfate; methyl sulfate; benzene sulfonate; alkoxy $(C_1-C_4)$ benzene sulfonate; alkyl $(C_1-C_3)$ benzene sulfonate, preferably a toluene sulfonate, such as p-toluene sulfonate; nitrate; phosphate; alkane sulfonate $(C_1-C_4)$; perchlorate, tetrafluoroborate, iodate; $Br_3^-$ and $I_3^-$; and $(C_6H_5)_4B^-$.

Illustrative of the acid residue, identified in Formula II above as . HB, which is suitable for use in the present invention are inorganic acids, such as HCl, HI, HBr, $HClO_4$, $H_2SO_4$, $HNO_3$ and $H_3PO_4$ and organic acids, such as $CH_3SO_3H$,

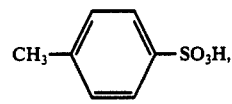

$ClCH_2COOH$, and other organic acids of sufficient acid strength to form stable salts with the

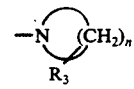

group.

With regard to the pyrazolium salts of Formula (I) above, it is to be understood that certain multivalent anions, such as sulfate or phosphate may have associated with them a cation in addition to the pyrazolium, as for example, a proton, or an alkali metal or akaline earth metal. For simplicity, such anions are characterized as being unionized, although they probably are further ionized in fact. Typical representations are: $NaSO_4^-$, $KPO_4^=$, $MgPO_4^-$, $HSO_4^-$ or $NaHPO_4^-$.

Preferred pyrazolium compounds represented by above-defined Formulas (I) and (II), respectively, are those compounds of said formulas wherein $R_1$ and $R_2$ are each methyl, $R_3$ is hydrogen or methyl, $R_4$ is hydrogen or n-propoxy, $R_5$ is phenyl or cyclohexyl; n is five, m is one or two and X is an anion with a charge of one.

Exemplary of the effective compounds of the present invention are:

1,2-Dimethyl-3-phenyl-5-piperidinopyrazolium iodide, hydroiodide
1,2-Diethyl-3-phenyl-5-piperidinopyrazolium perchlorate, hydroperchlorate
1,2-Dimethyl-3-phenyl-5-(1-pyrrolidinyl)pyrazolium methyl sulfate
3-(Hexahydro-1H-azepin-1-yl)-1,2-dimethyl-5-phenylpyrazolium iodide
1,2-Dimethyl-3-(4-methylpiperidino)-5-phenylpyrazolium iodide
1,2-Dimethyl-3-(2-methylpiperidino)-5-phenylpyrazolium iodide
1,2-Dimethyl-3-(3-methylpiperidino)5-phenylpyrazolium iodide
4-Bromo-1,2-dimethyl-3,5-dipiperidinopyrazolium bromide, hydrobromide
4-Bromo-1,2-dimethyl-3,5-dipiperidinopyrazolium perchlorate, hydroperchlorate
1,2-Dimethyl-3,5-dipiperidinopyrazolium bromide, hydrobromic acid salt
1,2-Dimethyl-3,5-dipiperidinopyrazolium perchlorate
1,2-Dimethyl-3-(3-methylpiperidino)-5-phenylpyrazolium perchlorate
1,2-Dimethyl-3-(3-methylpiperidino)-5-phenylpyrazolium bromide
1,2-Dimethyl-3-(3-methylpiperidion)-5-phenylpyrazolium methyl sulfate
1,2-Diethyl-3-(3-methylpiperidino)-5-phenylpyrazolium methyl sulfate 1,2-Dimethyl-3(3-piperidino)-5-phenylpyrazolium chloride 1,2-Dimethyl-3(2-methylpiperidino)-5-phenyl-pyrazolium methyl sulfate 3-Cyclohexyl-1,2-dimethyl-5-(3-methylpiperidino)-pyrazolium methyl sulfate (and chloride)

1,2-Dimethyl-3-(2-methylpiperidino)-5-phenyl-pyrazolium perchlorate 1,2-Dimethyl-3-(2-methylpiperidino)-5-phenyl-pyrazolium chloride, hydrochloride 3-Cyclohexyl-1,2-dimethyl-5-(3-methylpiperidino)-pyrazolium iodide 3-Cyclohexyl-1,2-dimethyl-5-piperidinopyrazolium iodide 1-Ethyl-2-methyl-3(p-fluorophenyl)-5-piperidinopyrazolium chloride 1,2-Dimethyl-3-(m-chlorophenyl)-4-chloro-5-(2-methylpiperidino)-pyrazolium chloride 4-Fluoro-1,2-dimethyl-3-phenyl-5-(3-methyl-piperidino)pyrazolium iodide 1,2-Dimethyl-3-phenyl-5-(3-methoxypiperidino)-pyrazolium iodide 1,2-Dimethyl-3-(3-ethylpiperidino)-5-phenyl-pyrazolium iodide 1,2-Dimethyl-3-(p-fluorophenyl)-5-piperidinopyrazolium iodide 1,2-Dimethyl-3-(3-methoxypiperidino)-5-phenyl-pyrazolium iodide 3-(4-Carboxypiperidino)-1,2-dimethyl-5-phenyl-pyrazolium iodide, ethyl ester 3-(4-Benzylpiperidino)-1,2-dimethyl-5-phenyl-pyrazolium iodide 1,2-Dimethyl-5-phenyl-3-(4-phenylpiperidino)-pyrazolium perchlorate 1,2-Dimethyl-5-phenyl-3-(4-phenylpiperidino)-pyrazolium iodide 1,2-Dimethyl-3-(4-methoxypiperidino)-5-phenyl-pyrazolium iodide 1,2-Dimethyl-3-(2-cyanopiperidino)-5-phenyl-pyrazolium iodide 1,2-Dimethyl-3-(2-propylpiperidino)-5-phenyl-pyrazolium iodide 1,2-Dimethyl-3-(2-carboxamidopiperidino)-5-phenyl-pyrazolium iodide 1-Ethyl-3-(3-methylpiperidino)-2-methyl-5-phenyl-pyrazolium ethyl sulfate 1-Ethyl-3-(3-methylpiperidino)-2-methyl-5-phenyl-pyrazolium tetraborofluorate 1-Ethyl-3-(2-methylpiperidino)-2-methyl-5-phenyl-pyrazolium tetrafluoroborate 1-Ethyl-3-(4-methylpiperidino)-2-methyl-5-phenyl-pyrazolium tetrafluoroborate 1-Ethyl-2-methyl-3-piperidino-5-phenylpyrazolium tetrafluoroborate In accordance with the process of the invention, formula (I) compounds defined above can be synthesized from an intermediate (IV), defined below, by the reaction of the intermediate 3-halopyrazolium compounds (IV) with a saturated azaheterocycle (III) hereinbelow defined within a temperature range of from about 20° C to about 100° C. In this reaction, it is necessary to include either 2 moles of the azaheterocycle, one as a base acceptor, or to employ 1 mole of azaheterocycle and one mole of another organic or inorganic base acceptor. In practice, tertiary amines, such as trimethylamine, triethylamine pyridine or quinoline can be employed. Alternatively, inorganic bases such as sodium bicarbonate and sodium carbonate are contemplated.

The reation is graphically illustrated in Method A as follows:

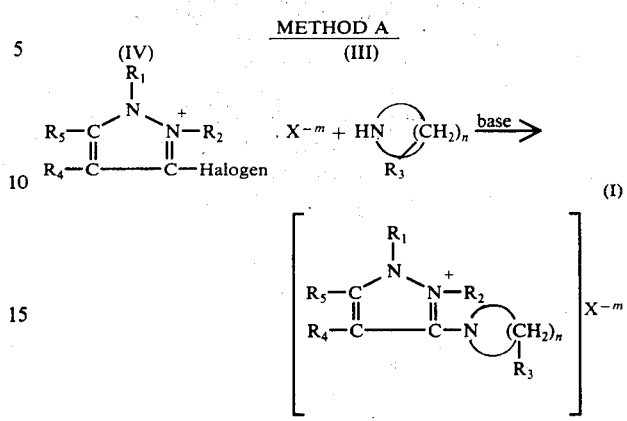

where $R_1$, $R_2$, $R_3$, $R_4$, $R_5$, $m$, $n$, and X are each as above defined. The foregoing reaction involves displacement of halogen by an azaheterocyclic group. Additionally, a variety of inert solvents can be utilized such as methanol, ethanol, propanol, dimethylformamide (DMF), acetone or acetonitrile. If desired, the azahetercyclic alone may be used also as the solvent.

It has been observed that a limitation to the aforementioned procedure is reaction temperature as well as reaction time. Heating compound (IV) with an excess of the above azaheterocycle, for instance, at temperatures above 100° C. for from 30 minutes (in the absence of a solvent) to about 24 hours (in the presence of a solvent), can cause an increase in the dealkylation of the pyrazolium compound (I) to the desired pyrazole. Thus, to prevent dealkylation, the preferred reaction temperature is 80° C., or less, and preferably from 40° to 80° C.

The counter ion X employed in the Method A above may be any of those ions set forth above. However, methyl sulfate, iodide, bromide, chloride, perchlorate, and tetrafluoroborate are preferred. The product, identified by formula (I) above, may be prepared with a particular anion X, either by reacting compound (IV) containing the required anion X, or by one of a plurality of alternative procedures outlined below. For instance, the anion of (I) may be replaced either by exchange chromatography as in Method A on an appropriately modified Dowex 1-X8 base anion exchanger or by the addition of a concentrated solution of an acid salt (Method A-salt), e.g. utilizing sodium iodide, sodium tetrafluoroborate, or sodium perchlorate [or 10% aqueous perchloric acid (Method A acid)], thereby causing the water insoluble salt to precipitate. When an acid is used as, for instance, perchloric acid, not only does ion exchange occur, but there also may occur the formation of a perchlorate salt of the azaheterocyclic group.

Purification of a formula (I) compound above-identified can be effected by dissolving said comound in water, excepting the water insoluble salts, such as perchlorate or iodide, and washing the aqueous layer with ether, discarding the ether layer, then extracting the same with chloroform or methylene chloride. Product (I) may then be precipitated from the chlorinated hydrocarbon by the addition of diethyl ether.

The preparation of 3-halopyrazolium compounds (IV) employed in Method A can be accomplished by the stepwise reactions of a benzoyl acetic acid ester or a cycloalkanoyl actic acid ester (V), defined more particularly hereinbelow, with hydrazine or an alkyl hydrazine to yield a pyrazolinone (VI), followed by the halogenation of said pyrazolinone (VI) with phosphorus oxyhalide to yield the corresponding 3-halopyrazole (VII) and, finally, alkylating said halopyrazole (VII) to yield the desired 3-halopyrazolium compound (IV). Conversion of the formula (IV) 3-halopyrazolium salt to the formula (I) pyrazolium salt containing the 3-nitrogen heterocyclic group is readily achieved by reaction of the halopyrazolium salt with an azaheterocycle in the presence of a base as above defined.

The overall reaction in four steps or operations can be graphically illustrated below with phosphorus oxychloride to represent the oxyhalide employed as the halogenation reagent of the pyrazolinone (VI).

tions will vary depending on the reactants employed. Reaction is effected by combining an alkylating agent and an halopyrazole usually in the presence of a solvent. The reaction mixture is heated until the reaction occurs. Where the alkylating reagents employed are volatile, such as methyl chloride, the reaction is preferably conducted in an autoclave, to avoid loss of the reactants. The quaternization of the formula (IV) 3-halopyrazolium compound is accomplished by utilizing an alkylating agent, such as dimethyl sulfate, methyl chloride or methyl iodide, alone or in the presence of a solvent.

The preparation of formula (IV) 3-halopyrazolium compounds where $R_4$ is halogen, can be accomplished by the direct known halogenation of the 1-alkyl-3-

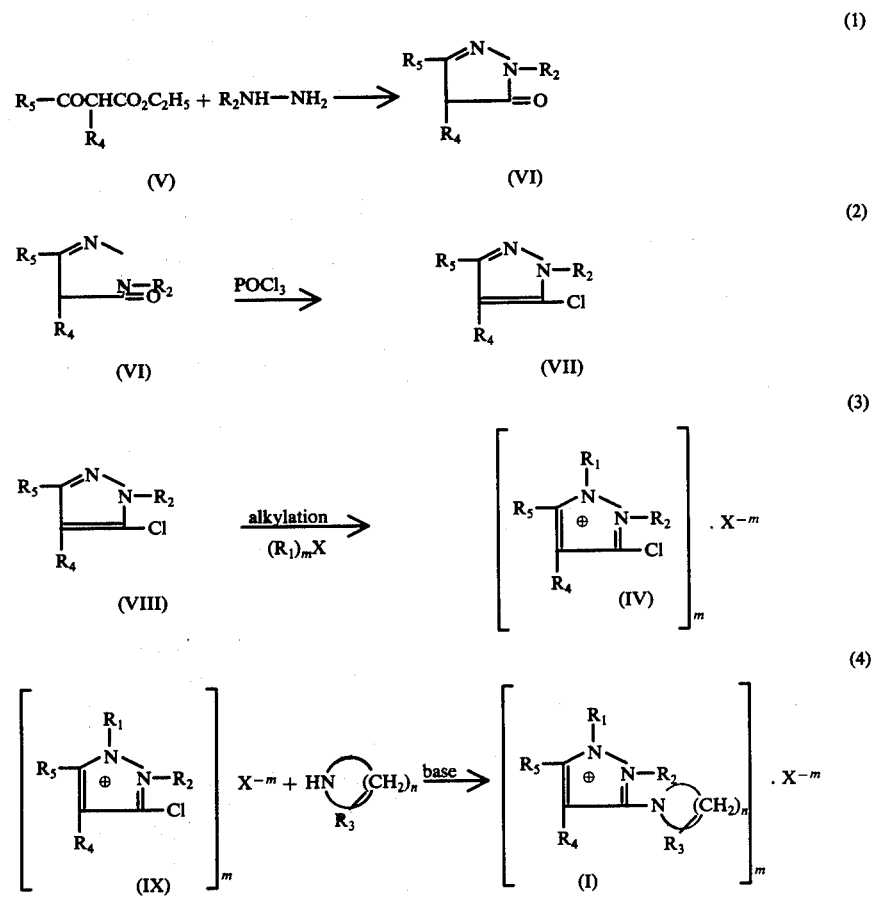

where $R_1$, $R_2$, $R_3$, $R_4$, $R_5$, X, m and n are each as above defined.

The alkylation reaction in Step (3) above is preferably conducted in the presence of a solvent, such as xylene, toluene, benzene, 1,2-dichloroethane or the like. Alternatively, it may be conducted with the exclusion of a solvent using solely the halopyrazole (VII) reactant and an alkylating agent.

Suitable and commercially available alkylating reagents include, for instance, alkyl sulfates, alkyl halides, alkyl perchlorate, alkyl hydrogen sulfate, or alkyl toluene sulfonates where the alkyl group contains from one to four carbon atoms, such as methyl, ethyl, n-propyl, n-butyl and homologues of the same.

In general, the halopyrazole and alkylating reagent combine on an equimolar basis. However, it is a good practice to employ an excess of the alkylating agent. Optimum reaction conditions for effecting the alkylahalopyrazole (VII) in acetic acid.

Compounds containing 3,5-disubstituted azaheterocyclic substituents (IX) can be prepared by a process, hereinafter referred to as Method B. This method involves the reaction of a 3,5-dihalopyrazolium compound with an azaheterocycle. Both 3- and 5-dihalogens react rapidly at ambient temperatures up to 80° C. However, under these conditions, the substituent in the 4-position, even a 4-halogen, is unreactive to an azaheterocycle. The reaction is preferably conducted in the presence of a base and an aprotic solvent such as xylene, toluene, benzene or the like. The overall "Method B" reaction is graphically illustrated as follows:

(VIII)

-continued

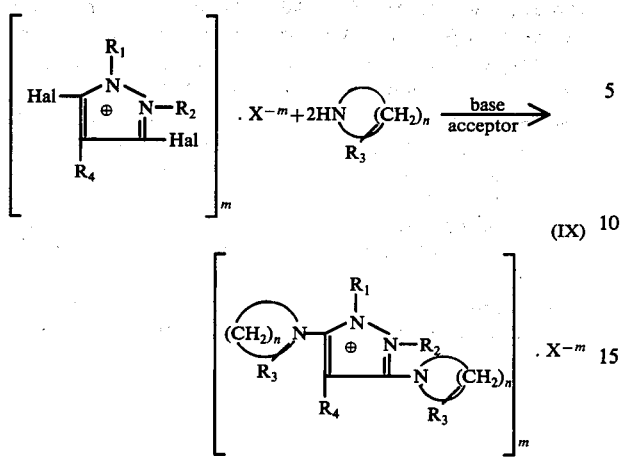

where $R_1$, $R_2$, $R_3$, $R_4$, $R_5$, X, $m$ and $n$ are each as above defined and Hal is a halogen substituent.

In practice, it has been found that formula (X) 3,5-diazaheterocyclylaminopyrazolium compounds, where $R_4$ is hydrogen, hereinbelow defined, can be advantageously prepared from formula (IX) 3,5-diazaheterocyclamino-4-halopyrazolium compounds by a dehalogenation process, hereinafter referred to as "Method C". The process involves the reaction of a 3,5-diazaheterocyclylamino-4-halopyrazolium salt (IX) with hydrogen, in the presence of a strong base such as an alkali metal alkoxide (e.g., sodium methoxide, sodium ethoxide or potassium t-butoxide) and a catalyst, such as palladium on carbon or platinum on carbon. The reaction is preferably conducted at a temperature between about 20° and 40° C. The "Method C" reaction is graphically illustrated as follows:

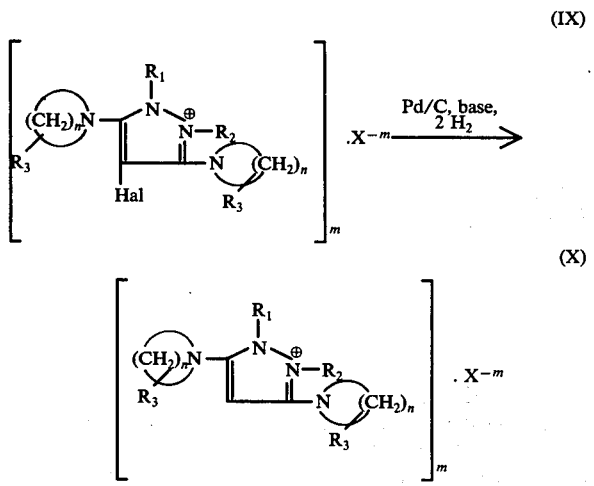

where $R_1$ to $R_5$, X, $m$, $n$ and X are the same as defined above.

In general, the compounds of the invention exhibit marked advantages over compounds, such as the known 1,2-dialkyl-3,5-pyrazolium salts, in that the compounds herein demonstrate both effective wild oats activity and good selectivity on wheat. Stated otherwise, the compounds of this invention are effective for controlling wild oats but are less phytotoxic to several varieties of wheat where injury has been observed with the known pyrazolium compounds.

For the postemergence control of undesirable plant species, the pyrazolium compounds of the present invention are applied to the foliage of said undesirable plants, generally as a liquid spray, in sufficient amounts to provide from about 0.28 kilogram to about 11.2 kilograms per hectare (kg/ha) and, preferably, 0.56 to 4.48 kg/ha of the active compound.

For application as liquid sprays, said compounds are generally prepared as wettable powders or emulsifiable concentrates which are dispersed in water or other inexpensive liquid diluent and applied as dilute solutions or suspensions to the foliage of plants.

Wettable powder formulation can be prepared by grinding together about 25 to 95%, by weight, of the formula (I) pyrazolium salt and a solid diluent, such as attapulgite, kaolin, or diatomaceous earth. The thus prepared solid formulation is admixed with about 1 to 5%, by weight, of a dispersing agent, such as the calcium salt of a polymerized alkyl aryl sulfonic acid, sodium lignosulfonate, or the sodium salt of condensed naphthalene sulfonic acid, and blending therewith about 1 to 5% by weight of a surfactant, such as alkyl phenoxy polyoxyethylene ethanol, sodium alkyl naphthalene sulfonate, or a polyoxyethylated vegetable oil. These wettable powder formulations are particularly desirable for use in formulating the pyrazolium (I) and (II) compounds.

Advantageously, these formulations provide effective control of broadleaf weeds and grass weeds, and are particularly effective against mustard, pigweed, tea weed, velvet leaf and wild oats.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of 1-Methyl-3-phenyl-2-pyrazolin-5-one

Ethyl benzoylacetate (1,538 g, 8 moles) dissolved in isopropanol (6 l) is placed in a 12 l flask under an atmosphere of nitrogen. Methylhydrazine (410 g, 8.7 moles) in isopropanol (800 ml) is added with stirring in a dropwise manner to the ethyl benzoylacetate solution prewarmed to about 80° C. During the addition external heating is removed. Seeding of the reaction mixture with the product at the point of one-third addition of methylhydrazine causes a copious precipitate of product. This procedure eliminates a large exotherm from occurring at a later stage. After the addition is completed, the reaction mixture is held at about 80° C. for 2 hours. Cooling the slurry to 20° C. and filtering off the solid, a yield of 1,131 g (81%) of product after drying and having a melting point of 211° C. is obtained.

EXAMPLE 2

Preparation of 5-Chloro-1-methyl-3-phenylpyrazole

To a solution of phosphorus oxychloride (2,015 g, 19 moles) is added solid 1-methyl-3-phenylpyrazolin-5-one (2,073 g, 11.9 moles) with stirring and warming. At 100° C. the mixture becomes homogeneous. The reflux temperature rises from 119° to 143° C. over a period of 30 hours. After cooling, the mixture is poured into ice and water (8 l) with stirring. After 4 hours the slurry is filtered and the filter cake added to 1 l of water containing 1.5 l of 10% sodium hydroxide solution with stirring. Removal of the solid by filtration followed by a recrystallization from hexane yields 1,523 g of product, having a melting point ranging from 61° to 62° C.

EXAMPLE 3

Preparation of
3-Chloro-1,2-dimethyl-5-phenylpyrazolium methyl sulfate utilizing one of two Methods

METHOD A

Dimethyl sulfate (30 g, 0.22 mole) is added to a stirred solution of 5-chloro-1-methyl-3-phenylpyrazole (39.5 g, 0.2 mole) in dry xylene (350 ml) and the reaction mixture is warmed to 105° to 115° C. for 18 hours. A brown syrup separates out, the reaction is cooled and the xylene is decanted off. Dry acetone (300 ml) is added and, after stirring, a white precipitate separates out and is filtered off to yield 33.8 g, (55%) whose melting point ranges from 100° to 102° C. Recrystallization from dry acetone-toluene yields white needles whose melting point ranges from 102° to 104° C.

Analysis calculated for $C_{12}H_{15}N_2ClSO_4$: C, 45.22; H, 4.74; N, 8.79; Cl, 11.13. Found: C, 45.31; H, 4.81; N, 8.93; Cl, 11,24.

METHOD B

To a solution of dimethyl sulfate (1,596 g, 12.66 moles) at 70° to 74° C. is added 5-chloro-1-methyl-3-phenylpyrazole (1,523 g, 7.912 moles). During the exothermic addition the heat source is removed. After the exothermic reaction has ceased, the reaction mixture is maintained at 80° C. by external heating for 2 hours and then is poured into toluene.

Toluene is decanted off, leaving a residual syrup, which is treated with additional toluene and decanted off as above. The syrup is dissolved in chloroform, filtered, and the filtrate evaporated to an oil, which crystallizes from acetone to yield 1.52 kg, (60.3%) mp 95° to 96° C.

EXAMPLE 4

Preparation of
3-Chloro-1,2-dimethyl-5-phenylpyrazolium iodide

To an aqueous solution of 3-chloro-1,2-dimethyl-5-phenylpyrazolium methyl sulfate is added a saturated aqueous solution of sodium iodide at 5° C. A copious precipitate is formed and filtered off. The solid is dissolved in methylene chloride and precipitated with diethyl ether to yield almost white crystals mp 162° to 164° C.

Analysis calculated for $C_{11}H_{12}N_2ClI$: C, 39.49; H, 3,62; N, 8.38; Cl, 10.64; I, 37.93. Found: C, 39.46; H, 3.61; N, 8.44; Cl, 10.47; I, 37.85.

EXAMPLE 5

Preparation of
3-cyclohexyl-1-methyl-2-pyrazolin-5-one

To ethyl β-oxocyclohexanepropionate (4.4 g, 0.234 mole) in n-propanol (500 ml) is added dropwise with stirring under nitrogen at 80° C. methylhydrazine (13.8 g, 0.3 mole). After heating at reflux during 5 hours, the reaction is cooled and evaporated to a residual oil. Crystallization from ethylacetate gives a white powder mp 170.5° to 172° C.

Analysis calculated for $C_{10}H_{10}N_2O$: C, 66.63 H, 8.95; N, 15.54. Found C, 66.59; H, 9.07; N, 15.69.

EXAMPLE 6

Preparation of
5-Chloro-3-cyclohexyl-1-methylpyrazole

Phosphorus oxychloride (15.3 g, 0.1 mole) is added to 3-cyclohexyl-1-methyl-2-pyrazolin-5-one and the mixture stirred and heated at 120° to 135° C. for 8 hours. The cooled reaction mixture is then poured into ice-water, made alkaline with 1% aqueous hydroxide and extracted with methylene chloride. Removal of solvent under reduced pressure, then in vacuo at 70° C. affords an oil, 8 g, (93.8%).

Analysis calculated for $C_{10}H_{15}N_2Cl$: C, 60.45; H, 7.61; N, 14.10; Cl, 17.85. Found: C, 60.28; H, 7.55; N, 14.20; Cl, 17.79.

EXAMPLE 7

Preparation of
3-Chloro-5-cyclohexyl-1,2-dimethylpyrazolium methyl sulfate [and hydrogen sulfate (1:1)]

A mixture of 5-chloro-3-cyclohexyl-1-methyl-pyrazole (7 g, .0352 mole) and dimethyl sulfate (8.82 g, 0.07 mole) is heated to 80° C. and the heating source then removed. the reaction temperature rises to 88° C. and then, after the exotherm, the temperature is maintained at 80° C. by external heating for 6 hours. Toluene (100 ml) is added to the cooled reaction and the mixture is set aside overnight at room temperature and then a waxy solid is filtered off. Crystallization from methylene chloride-ether affords a granular product, mp equal to 70° to 73.5° C., 11.2 g (100%). NMR and infrared spectra indicate a mixture of $CH_3SO_4$ and $HSO_4$ anions.

Analysis calculated for $C_{12}H_{21}N_2ClSO_4$ (as $CH_3SO_4$): C, 44.36; H, 6.57; N, 8.63; S, 9.87; Cl, 10.92. Found C, 41.34; H, 6.24; N, 8.14; S, 9.12; Cl, 10.31.

A portion of the above compound is readily converted to the corresponding perchlorate whose melting point ranges from 216° to 218° C.

EXAMPLE 8

Preparation of 3,4,5-Tribromo-1-methypyrazole

To 3,4,5-tribromopyrazole (4.5 g, 0.15 mole) at 3N aqueous sodium hydroxide (6 g, 0.15 mole) is added at room temperature with stirring dimethyl sulfate (19 g, 0.15 mole). After 10 minutes a solid separates out. An additional gram (0.0079 mole) of dimethyl sulfate is added and the mixture is stirred for 3 days, filtered, and the precipitate water washed and air dried to yield 33 g (73%), mp 85° to 86° C. Crystallization from cyclohexane gives desired solid product whose melting point ranges from 90° to 91° C.

Analysis calculated for $C_4H_3N_2Br_3$: C, 15.07; H, 0.95; N, 8.79; Br, 75.21. Found: C, 15.16; H, 0.82; N, 8.7; Br, 75.36.

EXAMPLE 9

Preparation of 3,4,5-Tribromo-1,2-dimethylpyrazolium methyl sulfate (and perchlorate)

A stirred suspension of 1-methyl-3,4,5-tribromopyrazole (19.3 g, 0.06 mole) in dimethyl sulfate (80 ml) is stirred and heated at 130° to 135° C. for 6 hours. On cooling and setting aside overnight, a solid is obtained and filtered off, benzene washed and air dried to yield 18.7 g, (70%) whose melting point ranges from 199° to 203° C.

Analysis calculated for C₆H₉N₂BR₃SO₄: C, 16.19; H, 2.04; N, 6.29; Br, 53.88; S, 7.20. Found: C, 16.19; H, 1.99; N, 6.38; Br, 53.98; S, 7.31.

Treatment of the above methyl sulfate compound with aqueous perchloric acid affords the perchlorate, mp 300° to 300.5° C.

EXAMPLE 10 Preparation of 1,2-Dimethyl-3-phenyl-5-piperidinopyrazolium iodide (and perchlorate), Employing Method A Piperdine (2.56 g, 0.03 mole) is added to 1,2-dimethyl-3-chloro-5-phenylpyrazolium methyl sulfate (4.77 g, 0.015 mole) in absolute ethanol (30 ml) and the mixture stirred with a bar magnet and heated under reflux for 4 hours. After cooling, the reaction mixture is evaporated under reduced pressure to a brown oil, and the dissolved in 50 ml of aqueous saturated sodium bicarbonate solution. The aqueous layer is extracted with ether and this organic layer discarded, then with chloroform. Evaporation of the chloroform layer affords 1,2-dimethyl-3-phenyl-5-piperidinopyrazolium methyl sulfate as a viscous oil. The oil is redissolved in water and saturated aqueous potassium iodide solution is added. An immediate copious white precipitate of 1,2-dimethyl-3-phenyl-5-piperidinopyrazolium iodide is formed, then filtered and washed with ice cold water to give 3.37 g, (56%) of product having a melting point ranging from 179° to 180° C. The melting point is unchanged by dissolving in chloroform, filtering and reprecipitating with diethyl ether and filtering off the solid. The analysis of resultant product is set forth below in Table I, compound 1, following Example 12, hereinbelow.

Treatment of a portion of the iodide compound dissolved in warm water with 10 % aqueous perchloric acid yields a white solid, which after cooling to 10° C. is filtered off, mp 137° to 138° C., whose analysis is set forth below in Table I, compound 2, following Example 12 below. Alternatively, the latter compound can also be obtained directly by treating an aqueous solution of the methyl sulfate derivative above, with 10% sodium perchlorate and filtering off the product.

EXAMPLE 11 Preparation of 1,2-Dimethyl-3,5-dipiperidinopyrazolium bromide Employing Method C 4-Bromo-1,2-dimethyl-3,5-dipiperidinopyrazolium bromide (6.3 g, 0.015 mole) is dissolved in methanol (150 ml) and sodium hydroxide (1.2 g, 0.3 mole) and treated with 10% palladium on carbon. The mixture is hydrogenated at 25° C. and absorbs hydrogen (290 ml) in 25 minutes. The catalyst is filtered off, washed with ethanol and aqueous hydrogen bromide (10 ml) is added. The mixture is evaporated in vacuo to an oil, which is dissolved in chloroform and precipitated with diethyl ether to yield a white powder of filtration mp 211° to 212° C., 3.4 (69%). Resultant listed compound 10, in Table I below following Example 12 is analyzed and the results thereof is reported in said Table.

An aliquot amount of the above bromide is dissolved in water and converted with 10% perchloric acid in quantitative yield to the perchlorate derivative having a melting point ranging from 171° to 172° C, and an analysis set forth in Table I below, designated as compound 11.

EXAMPLE 12

Following the procedure of Method A or Method B hereinabove defined, compounds which are identified in Table I below are set forth along with their analysis.

Table I

Preparation of  . $X^{-m}$

| No. | $R_3$ | X | $R_4$ | $R_5$ | Method | (%) Yield | (° C) mp | Analysis Calculated | %Found |
|---|---|---|---|---|---|---|---|---|---|
| 1 |  | I⁻ | H |  | A<br>A salt(NaI on intermediate (CH₃SO₄) | 56 | 179–180 | C 30.14<br>H 5.80<br>N 10.96 | C 49.74<br>H 5.65<br>N 10.91 |
| 2 |  | ClO₄⁻ | H |  | A<br>A acid(HClO₄ on intermediate (CH₃SO₄) | 95 | 137–138 | C 54.01<br>H 6.23<br>N 11.80 | C 53.86<br>H 6.07<br>N 11.77 |
| 3 |  | CH₃SO₄⁻ | H |  | A | 63 | 112–114 | C 55.57<br>H 6.86<br>N 11.44 | C 55.14<br>H 6.70<br>N 12.17 |
| 4 |  | I⁻ | H |  | A | 75 | 122–124.5 | C 51.40<br>H 6.09<br>N 10.58 | C 51.39<br>H 6.23<br>N 10.38 |

Table I-continued

Preparation of $\left[\begin{array}{c} R_5 \\ R_4 \end{array} \underset{\oplus}{\overset{CH_3}{\underset{N}{N}}} \underset{R_3}{\overset{CH_3}{\underset{(CH_2)_n}{N}}}\right]_m \cdot X^{-m}$

| No. | $\underset{R_3}{N-(CH_2)_n}$ | X | R₄ | R₅ | Method | (%) Yield | (°C) mp | Analysis Calculated | %Found |
|---|---|---|---|---|---|---|---|---|---|
| 5 | 4-methylpiperidine | I⁻ | H | phenyl | A | 45 | 184.5–185 | C 51.40<br>H 6.09<br>N 10.58 | C 51.30<br>H 6.07<br>N 10.55 |
| 6 | 2-methylpiperidine | I⁻ | H | phenyl | A | 51 | 151–152 | C 51.40<br>H 6.09<br>N 10.58 | C 51.07<br>H 6.13<br>N 10.74 |
| 7 | 3-methylpiperidine | I⁻ | H | phenyl | A | 51 | 143–144.5 | C 51.40<br>H 6.09<br>N 10.58 | C 50.38<br>H 6.08<br>N 10.54 |
| 8 | piperidine | Br⁻ | Br | piperidinyl | B | 88 | 170–170.5 | C 42.67<br>H 6.21<br>N 13.27<br>Br 37.85 | C 42.77<br>H 45.98<br>N 13.26<br>Br 37.98 |
| 9 | piperidine | ClO₄⁻ | Br | piperidinyl | B Acid(HClO₄ on Br⁻) | — | 154–155 | C 40.77<br>H 5.93<br>N 12.68<br>Br 18.09 | C 40.79<br>H 6.01<br>N 12.77<br>Br 18.14 |
| 10 | piperidine | Br⁻ | H | piperidinyl | B Hydrogenation (Pd/C/H₂NaOH) on Compound 9 | 69 | 211–212 | C 52.48<br>H 7.93<br>N 16.32<br>Br 23.28 | C 52.3<br>H 7.66<br>N 16.04<br>Br 22.64 |
| 11 | piperidine | ClO₄⁻ | H | piperidinyl | B HClO₄ on compound 10 | 95 | 170–171 | C 49.6<br>H 7.50<br>N 15.44 | C 49.38<br>H 7.68<br>N 15.00 |
| 12 | 3-methylpiperidine | ClO₄⁻ | H | pyridyl | A Acid(HClO₄ on compound 14 the CH₃SO₄⁻) | 54 | 110–112 | C 55.21<br>H 6.54<br>N 11.36 | C 54.01<br>H 6.51<br>N 10.92 |
| 13 | 4-methylpiperidine | Br⁻ | H | phenyl | A Acid(HBr on compound 14 the CH₃SO₄⁻) | 60 | 144–146 | C 58.28<br>H 6.91<br>N 11.99 | C 57.92<br>H 6.77<br>N 11.89 |
| 14 | 3-methylpiperidine | CH₃SO₄⁻ | H | phenyl | A | 67 | glass | C 56.68<br>H 7.14<br>N 11.02 | C 56.39<br>H 7.15<br>N 11.20 |
| 15 | 3-methylpiperidine | Cl⁻ · 2H₂O | H | phenyl | Ion exchange on Dowex 1-X8-Cl anion, using compound 14, CH₃SO₄⁻ | 47 | 70.5–72 | C 59.90<br>H 8.66<br>N 11.67<br>Cl 11.61 | C 60.64<br>H 8.11<br>N 12.58<br>Cl 10.21 |

Table I-continued

Preparation of $\left[\begin{array}{c}\text{imidazolinium structure with } R_5, R_4, N\text{-}CH_3, N\text{-}CH_3, N(CH_2)_nR_3\end{array}\right]_m \cdot X^{-m}$

| No. | N–(CH$_2$)$_n$–R$_3$ | X | R$_4$ | R$_5$ | Method | (%) Yield | (° C) mp | Analysis Calculated | %Found |
|---|---|---|---|---|---|---|---|---|---|
| 16 | 2-methylpiperidinyl | CH$_3$SO$_4^-$ | H | phenyl | A | 67 | glass | C 56.68<br>H 7.14<br>N 11.02 | C 55.07<br>H 7.09<br>N 10.60 |
| 17 | 2-methylpiperidinyl · HCl | Cl$^-$ | H | phenyl | Ion exchange on Dowex 1-X8-Cl anion using compound 16 | 60 | oil | N 12.27<br>Cl 20.72 | N 11.70<br>Cl 19.92 |
| 18 | 2-methylpiperidinyl | ClO$_4^-$ | H | phenyl | A Salt NaClO$_4$ on compound 16 | — | 94–95 | C 55.21<br>H 6.54<br>N 11.36 | C 54.94<br>H 6.48<br>N 11.38 |
| 19 | 4-methylpiperidinyl | CH$_3$SO$_4^-$<br>Cl$^-$ (75:25) | H | phenyl | A | 98 | glass | C* 55.78<br>H* 8.98<br>N* 10.84<br>S* 8.27<br>Cl — | *[as CH$_3$SO$_4$]<br>C 51.91<br>H 8.16<br>N 10.38<br>S 6.83<br>Cl 2.56 |
| 20 | 4-methylpiperidinyl | I$^-$ | H | phenyl | A Salt · NaI on compound 19 | — | glass | C 50.68<br>H 7.59<br>N 10.42<br>I 31.47 | C 50.59<br>H 7.89<br>N 10.42<br>I 30.60 |
| 21 | 3-methylpiperidinyl | I$^-$ | H | phenyl | A Salt · NaI on CH$_3$SO$_4^-$ salt | — | 99–100 | C 49.39<br>H 7.24<br>N 10.89<br>I 32.68 | C 47.99<br>H 7.24<br>N 10.42<br>I 31.61 |
| 22 | 3-methylpiperidinyl | I$^-$ | Br | phenyl | A | 75 | 193–194 | C 42.87<br>H 4.87<br>N 8.82<br>Br 16.78<br>I 26.65 | C 42.81<br>H 4.33<br>N 8.82<br>Br 16.90<br>I 26.68 |
| 23 | 4-methylpiperidinyl | I$^-$ | Br | phenyl | A | 63 | 211–213 | C 42.87<br>H 4.87<br>N 8.82<br>Br 16.78<br>I 26.65 | C 42.58<br>H 5.00<br>N 8.78<br>Br 16.89<br>I 26.56 |
| 24 | 2-methylpiperidinyl | ClO$_4^-$ | Br | phenyl | A | 6 | 197–199 | N 9.20 | N 8.91 |
| 25 | piperidinyl | I$^-$ | Br | phenyl | A | 16 | 201–202 | C 41.58<br>H 4.58<br>N 9.09<br>Br 17.29 | C 39.15<br>H 4.38<br>N 8.66<br>Br 16.39 |
| 26 | 2-phenyl-tetrahydropyridinyl | I$^-$ | H | phenyl | A | 56 | 202–203 | C 57.52<br>H 5.70<br>N 9.15 | C 57.56<br>H 5.84<br>N 9.17 |

Table I-continued

Preparation of $\left[\begin{array}{c} R_5 \underset{R_4}{\overset{CH_3}{\underset{\oplus}{N}}}\overset{N-CH_3}{\underset{N}{\parallel}} \\ \phantom{R_4}\overset{\phantom{}}{R_3}(CH_2)_n \end{array}\right]_m \cdot X^{-m}$

| No. | $\underset{R_3}{\overset{N\ (CH_2)_n}{\mid}}$ | X | $R_4$ | $R_5$ | Method | (%) Yield | (° C) mp | Analysis Calculated | %Found |
|---|---|---|---|---|---|---|---|---|---|
| 27 | N—⟨piperidine-CH(phenyl)⟩ | ClO₄ | H | phenyl | A Salt · NaClO₄ on compound 26 | — | 207–208 | C 58.72 H 6.27 N 9.34 | C 58.38 H 5.91 N 8.70 |
| 28 | N—⟨piperidine-CH₂-phenyl⟩ | I⁻ | H | phenyl | A | 66 | 123–125 | C 58.36 H 5.96 N 8.88 | C 57.94 H 6.05 N 8.70 |
| 29 | N—⟨piperidine-OCH₃⟩ | I⁻ | H | phenyl | A | 87 | 52–55 | C 50.12 H 7.76 N 9.23 | C 49.95 H 5.97 N 10.14 |
| 30 | N—⟨piperidine-OCH₃⟩ | I⁻ | H | phenyl | A | 44 | 176–177 | | |
| 31 | N—⟨piperidine-CO₂C₂H₅⟩ | I⁻ | H | phenyl | A | 95 | 106.5–107 | | |
| 32 | N—⟨piperidine-CONH₂⟩ | I⁻ | H | phenyl | A | 46 | 175–176 | | |

EXAMPLE 13

The postemergence herbicidal activity of the compounds of the present invention id demonstrated by the following tests, wherein a variety of nonocotyledonous and dicotyledonous plants are treated with test compounds dispersed in aqueous acetone mixtures. In the tests, seedling plants are grown in jiffy flats for about 2 weeks. The test compounds are dispersed in 50/50 acetonewater mixtures containing 0.5% Tween®20, a polyoxyethylene sorbitan monolaurate surfactant of Atlas Chemical Industries, in sufficient quantity to provide the equivalent of about 0.56 to 11.2 kg per hectare of active compound when applied to the plants through a spray nozzle operating at 40 psi for a predetermined time. After sprying, the plants, are placed on greenhouse benches and are cared for in the usual manner, commensurate with conventional greenhouse practices. two weeks after treatment, the seedling plants, with the exception of wild oats which are rated 5 weeks, are examined and rated according to the rating system provided below. The data obtained are reported in Table II below.

TABLE II

| Rating System: | % Difference in Growth From the Check* |
|---|---|
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over-all effect less than a 5 on the rating scale. | |

*Based on visual determination of stand, size, vigor, chlorosis, growth malformation and over-all plant appearance.

Plant Abbreviations:
LA — Lambsquarters (*Chenopodium album*)
MU — Mustard (*Brassica kaber*)
PI — Pigween (*Amaranthus retroflexus*)
RW — Ragweed (*Ambrosia artemisiifolia*)
MG — Morningglory (*Ipomoea purpurea)*
BA — Barnyardgrass (*Echinochloa crusgalli*)
CR — Crabgrass (*Digitaria sanguinalis*)
FO — Green Foxtail (*Setaria viridis*)
WO — Wild Oats (*Avena fatua*)
TW — Teaweed (*Sida spinosa*)
VL — Velvetleaf (*Abutilon theophrasti*)

Table II

| Structure | Treatment kg/ha | LA | MU | PI | RW | MG | BA | CR | FO | WO | TW | VL |
|---|---|---|---|---|---|---|---|---|---|---|---|---|
| Postemergence Herbicidal Activity | | | | | | Annual Weeds | | | | | | |
| 1,2-Dimethyl-3-(3-methyl-piperidino)-5-phenylpyrazo-lium chloride | 11.2 | | 9 | 9 | 1 | 8 | 8 | 3 | 3 | 9 | 9 | 9 |
| | 4.48 | | | 9 | | 9 | | 3 | 2 | 8 | 9 | 9 |
| 1,2-Dimethyl-3-(2-methyl-piperidino)-5-phenylpyrazo-lium methyl sulfate | 11.2 | | 7 | 8 | 0 | 5 | 7 | 3 | 1 | 9 | 8 | 8 |
| 1,2-Dimethyl-3-(2-methyl-piperidino)-5-phenylpyrazo-lium chloride, hydrochloride | 11.2 | | 8 | 9 | 1 | 5 | 7 | 3 | 1 | 9 | 7 | 9 |
| 1,2-Dimethyl-3-(2-methyl piperidino)-5-phenylpyrazo-lium perchlorate | 11.2 | | 8 | 9 | 0 | 9 | 7 | 2 | 1 | 9 | 9 | 8 |
| 3-Cyclohexyl-1,2-dimethyl-5-(3-methylpiperidino)pyrazo-lium methylsulfate (and chloride) | 11.2 | | 9 | 9 | 0 | 8 | 7 | 4 | 1 | 9 | 9 | 9 |
| 3-Cyclohexyl-1,2-dimethyl-5-(3-methylpiperidino)-pyrazolium iodide | 11.2 | | 9 | 9 | 0 | 9 | 8 | 7 | 7 | 9 | 9 | 9 |
| 3-Cyclohexyl-1,2-dimethyl-5-piperidinopyrazolium iodide | 11.2 | | 9 | 9 | 0 | 7 | 4 | 6 | 5 | 9 | 9 | 9 |
| 1,2-Dimethyl-3-phenyl-5-piperidinopyrazolium iodide | 4.48 | | 9 | 9 | | 3 | 5 | 9 | 3 | 9 | | 7 |
| | 1.12 | | 3 | 9 | | 1 | 1 | 7 | 0 | 8 | | 1 |
| | 0.56 | | 2 | 3 | | 1 | 1 | 6 | 0 | 8 | | 1 |
| 1,2-Dimethyl-3-phenyl-5-piperidinopyrazolium perchlorate | 4.48 | | 9 | 9 | | 3 | 6 | 9 | 1 | 9 | | 3 |
| | 1.12 | | 7 | 7 | | 1 | 1 | 7 | 1 | 8 | | 1 |
| | 0.56 | | 3 | 7 | | 1 | 1 | 6 | 0 | 8 | | 0 |
| 1,2-Dimethyl-3-phenyl-5-(1-pyrrolidinyl)pyrazo-lium methyl sulfate | 4.48 | | 9 | 9 | | 8 | 6 | 8 | 1 | 6 | | 9 |
| | 1.12 | | 6 | 8 | | 2 | 1 | 0 | 0 | 2 | | 9 |
| 3-(Hexahydro-1H-azepin-1-yl)-1,2-dimethyl-5-phenylpyrazolium iodide | 4.48 | | 9 | 9 | | 5 | 3 | 0 | 1 | 0 | | 3 |
| 1,2-Dimethyl-3-(4-methyl-piperidino)-5-phenylpyrazo-lium iodide | 4.48 | | 9 | 9 | | 5 | 4 | 0 | 1 | 8 | | 5 |
| | 1.12 | | 7 | 7 | | 2 | 4 | 0 | 0 | 9 | | 1 |
| 1,2-Dimethyl-3-(2-methyl-piperidino)-5-phenylpyrazo-lium iodide | 4.48 | | 9 | 9 | | 3 | 1 | 1 | 0 | 6 | | 5 |
| | 1.12 | | 9 | 9 | | 3 | 1 | 0 | 0 | 7 | | 5 |
| 1,2-Dimethyl-3-(3-methyl-piperidino)-5-phenylpyrazo-lium iodide | 4.48 | | 9 | 9 | | 3 | 5 | 1 | 1 | 6 | | 9 |
| | 1.12 | | 9 | 9 | | 5 | 2 | 1 | 0 | 7 | | 5 |
| 4-Bromo-1,2-dimethyl-3,5-dipiperidinopyrazolium perchlorate | 4.48 | | 9 | 9 | | 7 | 0 | 0 | 0 | 7 | | 3 |
| | 1.12 | | 9 | 9 | | 7 | 0 | 0 | 0 | 6 | | 3 |
| | 0.56 | | 9 | 9 | | 5 | 0 | 0 | 0 | 3 | | 3 |
| 4-Bromo-1,2-dimethyl-3,5-dipiperidinopyrazolium bromide | 4.48 | | 9 | 9 | | 9 | 3 | 7 | 8 | 7 | | 9 |
| | 1.12 | | 9 | 9 | | 8 | 1 | 5 | 1 | 6 | | 6 |
| | 0.56 | | 9 | 9 | | 6 | 1 | 0 | 0 | 3 | | 5 |
| 1,2-Dimethyl-3,5-dipiperi-dinopyrazolium bromide | 3.36 | 9 | 9 | 9 | 3 | 9 | 7 | 8 | 6 | 7 | | 9 |
| | 1.12 | 9 | 7 | 7 | 0 | 3 | 3 | 7 | 3 | 4 | | 3 |
| 1,2-Dimethyl-3,5-dipiperi-dinopyrazolium perchlorate | 5.60 | 9 | 9 | 9 | 1 | 2 | 1 | 3 | 5 | 8 | | 7 |
| 1,2-Dimethyl-3-(3-methyl-piperidino)-5-phenylpyrazo-lium bromide | 11.2 | 9 | 9 | 9 | 2 | 9 | 7 | 3 | 8 | 8 | | 9 |
| | 4.48 | | | 9 | | 9 | | 2 | 1 | 7 | 9 | 7 |
| 1,2-Dimethyl-3-(3-methyl-piperidino)-5-phenylpyrazo-lium perchlorate | 11.2 | 9 | 9 | 9 | 9 | 8 | 9 | 3 | 7 | 9 | | 9 |
| | 4.48 | | | 9 | | 7 | | 3 | 2 | 6 | 7 | 5 |
| 1,2-Dimethyl-3-(3-methyl-piperidino)-5-phenylpyrazo-lium methyl sulfate | 11.2 | | 9 | 9 | 0 | 9 | 8 | 6 | 9 | 7 | 9 | 9 |
| | 4.48 | | 9 | | 8 | | 2 | 1 | 7 | 7 | 8 | |
| 4-Bromo-1,2-dimethyl-5-(3-methylpiperidino)-3-phenyl-pyrazolium iodide | 11.2 | | 9 | 9 | 9 | 5 | 6 | 4 | 5 | 9 | 9 | 9 |
| | 4.48 | | 9 | 8 | 2 | 6 | 7 | 7 | 8 | 5 | 9 | 8 |
| 4-Bromo-1,2-dimethyl-5-(4-methylpiperidino)-3-phenyl-pyrazolium iodide | 11.2 | | 9 | 6 | 8 | 3 | 6 | 4 | 6 | 9 | 9 | 6 |
| | 4.48 | | 9 | 3 | 5 | 5 | 7 | 2 | 1 | 9 | 6 | 7 |
| 4-Bromo-1,2-dimethyl-3-phenyl-5-piperidinopyrazolium iodide | 11.2 | | 9 | 9 | 9 | 3 | 6 | 4 | 7 | 9 | 9 | 9 |
| | 4.48 | | 9 | 9 | 9 | 5 | 7 | 5 | 5 | 5 | 5 | 9 |

EXAMPLE 14

The selective postemergence effectiveness of the compounds of the present invention for controlling wild oats in the presence of wheat is demonstrated by the following tests. In these tests seedling plants of wild oats and several varieties of wheat, growing in separate pots, are sprayed with solutions or suspensions of test compound dispersed in 50/50 acetone/water mixtures containing b 0.5% Tween®20, a polyoxyethylene sorbitan monolaurate, in sufficient quantity to provide the equivalent of about 0.28 to 4.48 kg per hectare of active comound when applied to the plants through a spray nozzle operating at 40 psi for a predetermined time. Two or three replicates per treatment are used. After spraying, the plants are placed on greenhouse benches and cared for in the usual manner, commensurate with conventional greenhouse practices. Five weeks after treatment the seedling plants are examined and rated according to the rating system described in Example 5. Data obtained are reported in Table III below and show that the compounds of the subject invention are highly selective especially for wheat varieties, such as Era, Lark and Bonanza.

Wheat varieties employed in these tests include: Era, Lark, Bonanza, Waldron, Olaf, Genesee.

Compounds listed in Table III are especially preferred because of their wheat selectivity.

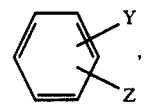

Table III

Postemergence Wild Oats Control in the Presence of Wheat

| Compound | Rate kg/ha | Waldron | Lark | Bonanza | Olaf | Genesee | Era | Wild Oats |
|---|---|---|---|---|---|---|---|---|
| 3-Cyclohexyl-1,2-dimethyl--5-(3-methylpiperidino)-pyrazolium methyl sulfate (and chloride) | 4.48 | | 0 0 0 | 0 5 0 | | | 1 1 1 | 3 6 3 |
| | 1.12 | | 0 0 0 | 0 0 0 | | | 1 1 1 | 3 6 6 |
| | 0.56 | | 0 0 0 | 0 0 0 | | | C 0 0 | 6 7 7 |
| 3-Cyclohexyl-1,2-dimethyl--5-piperidinopyrazolium iodide | 4.48 | | 1 1 1 | 1 0 0 | | | 2 3 7 | 6 8 8 |
| | 1.12 | | 0 0 0 | 0 0 0 | | | 2 2 2 | 6 8 9 |
| | 0.56 | | 0 0 0 | 0 0 0 | | | 3 2 2 | 7 8 8 |
| 1,2-Dimethyl-3-(2-methyl-piperidino)-5-phenylpyrazolium methyl sulfate | 4.48 | | 5 3 3 | 3 2 2 | | | 0 0 0 | 6 7 5 |
| | 1.12 | | 3 3 3 | 3 2 2 | | | 0 0 0 | 8 8 9 |
| | 0.56 | | 0 5 0 | 1 3 0 | | | 0 0 0 | 8 8 8 |
| | 0.28 | | 0 0 0 | 0 0 0 | | | 0 0 0 | 8 7 7 |
| 1,2-Dimethyl-3-(2-methyl-piperidino)-5-phenylpyrazolium perchlorate | 1.12 | | 6 6 5 | 3 3 3 | | | 0 0 0 | 9 9 8 |
| | 0.56 | | 0 5 6 | 1 3 3 | | | 0 0 0 | 9 8 9 |
| | 0.28 | | 0 0 0 | 0 0 0 | | | 0 0 0 | 9 9 8 |
| 1,2-Dimethyl-3-(2-methyl-piperidino)-5-phenylpyrazolium chloride,hydrochloride | 1.12 | | 3 5 1 | 2 3 1 | | | 0 0 0 | 8 9 9 |
| | 0.56 | | 0 5 0 | 0 3 0 | | | 0 0 0 | 9 9 9 |
| | 0.28 | | 0 0 0 | 0 0 0 | | | 0 0 0 | 6 6 9 |
| 1,2-Dimethyl-3-(3-methyl-piperidino)-5-phenylpyrazolium chloride | 1.12 | | 5 7 6 | 5 7 3 | | | 0 0 0 | 9 7 7 |
| | 0.56 | | 5 7 6 | 5 0 3 | | | 0 0 0 | 9 9 9 |
| | 0.28 | | 0 0 0 | 0 0 0 | | | 0 0 0 | 9 8 8 |
| 1,2-Dimethyl-3-(3-methyl-piperidino)-5-phenylpyrazolium methyl sulfate | 1.12 | | 7 6 6 | 5 6 5 | | | 0 0 0 | 8 8 7 |
| | 0.56 | | 0 3 2 | 0 2 2 | | | 0 0 0 | 9 9 8 |
| | 0.28 | | 0 0 0 | 0 0 0 | | | 0 0 0 | 9 9 9 |
| 1,2-Dimethyl-3-(3-methyl-piperidino)-5-phenylpyrazolium iodide | 1.12 | 0 1 | 6 7 6 | 6 5 3 | 0 0 | 0 | 0 0 0 | 8 7 8 |
| | 0.56 | 0 0 | 5 6 5 | 5 3 3 | 0 0 | 0 | 0 0 0 | 8 9 8 |
| | 0.28 | 0 0 | 0 2 0 | 0 0 0 | 0 0 | 0 | 0 0 0 | 9 8 8 |
| 1,2-Dimethyl-3-(2-methyl-piperidino)-5-phenylpyrazolium iodide | 1.12 | 2 0 | 2 2 | 3 3 | 2 1 | 0 | | 8 8 8 |
| | 0.56 | 2 2 | 2 2 | 0 2 | 2 2 | 0 | | 8 8 7 |
| | 0.28 | 0 0 | 0 0 | 0 7 | 0 0 | 0 | | 3 7 3 |
| 1,2-Dimethyl-3-(4-methyl-piperidino)-5-phenylpyrazolium iodide | 1.12 | 3 3 | 3 5 | 2 6 | 5 3 | 2 | | 9 8 8 |
| | 0.56 | 3 3 | 3 2 | 3 6 | 3 5 | 2 | | 9 8 8 |
| | 0.28 | 3 3 | 2 1 | 3 3 | 2 2 | 0 | | 7 8 7 |
| 1,2-Dimethyl-3-phenyl-5-piperidinopyrazolium iodide | 1.12 | 3 3 | 1 5 | 2 2 | 2 3 | 0 | | 8 8 8 |
| | 0.56 | 3 3 | 2 5 | 2 6 | 3 2 | 1 | | 9 9 8 |
| | 0.28 | 3 2 | 3 2 | 2 3 | 0 1 | 0 | | 7 9 8 |

We claim:

1. A compound having a formula selected from the group consisting of:

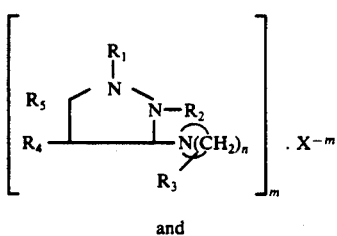

and

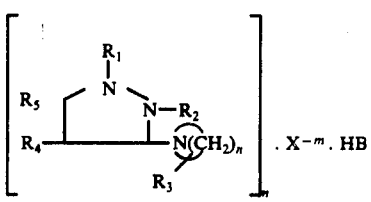

wherein $R_1$ and $R_2$ each represents alkyl ($C_1$-$C_4$); $R_3$ represents a member selected from the group consisting of hydrogen alkyl ($C_1$-$C_3$), alkoxy ($C_1$-$C_3$), phenyl, benzyl, cyano, carboxamido and carboxy; $R_4$ represents a member selected from the group consisting of hydrogen, alkoxy ($C_1$-$C_4$) and halogen; $R_5$ represents a member selected from the group consisting of cyclohexyl and

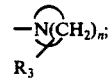

Y and Z each independently represents a member selected from the group consisting of hydrogen, halogen, methyl and -alkoxy ($C_1$-$C_4$); X represents a nonphytotoxic anion with a charge of 1 to 3; n represents an integer from 4 to 6; m represents an integer from 1 to 2; and HB is an inorganic acid.

2. The compound according to claim 1 wherein said compound is: 1,2-dimethyl-3-phenyl-5-piperidinopyrazolium iodide, hydroiodide.

3. The compound according to claim 1 wherein said compound is: 1,2-dimethyl-3-phenyl-5-piperidinopyrazolium perchlorate, hydroperchlorate.

4. The compound according to claim 1 wherein said compound is: 1,2-dimethyl-3-phenyl-5-(1-pyrrolidinyl)-pyrazolium methyl sulfate.

5. The compound according to claim 1 wherein the compound is: 3-(hexahydro-1H-azepin-1-yl)-1,2-dimethyl-5-phenylpyrazolium iodide.

6. The compound according to claim 1 wherein the compound is: 1,2-dimethyl-3-(4-methylpiperidino)-5-phenylpyrazolium iodide.

7. The compound according to claim 1 wherein the compound is: 1,2-dimethyl-3-(2-methylpiperidino)-5-phenylpyrazolium iodide.

8. The compound according to claim 1 wherein the compound is: 4-bromo-1,2-dimethyl-3,5-dipiperidinopyrazolium bromide, hydrobromide.

* * * * *